United States Patent [19]

Mast

[11] 4,140,656

[45] Feb. 20, 1979

[54] ANHYDROUS CLEAR GEL FACIAL CLEANSER

[75] Inventor: Rolf Mast, Scottsdale, Ariz.

[73] Assignee: Armour-Dial, Inc., Phoeniz, Ariz.

[21] Appl. No.: 840,209

[22] Filed: Oct. 7, 1977

[51] Int. Cl.$^2$ .................. C11D 7/24; C11D 17/00; A01N 9/00
[52] U.S. Cl. .................. 252/545; 252/89 R; 252/316; 252/DIG. 2; 252/DIG. 5; 252/DIG. 17; 424/81; 424/358
[58] Field of Search .................. 252/89, 162, 170, 171, 252/316, 545, DIG. 2, DIG. 5, DIG. 17; 424/81, 358

[56] References Cited

U.S. PATENT DOCUMENTS

| | | | |
|---|---|---|---|
| 3,101,301 | 8/1963 | Siegal | 252/316 X |
| 3,277,013 | 10/1966 | Gianladis | 252/153 |
| 3,427,382 | 2/1969 | Haefele | 424/71 |
| 3,499,844 | 3/1970 | Kibbel et al. | 252/316 |
| 3,507,806 | 4/1970 | Barker et al. | 252/316 |
| 3,645,904 | 2/1972 | Beach | 252/89 |
| 3,795,624 | 3/1974 | Feinstone | 252/91 |
| 3,876,771 | 4/1975 | Denner | 424/78 |

FOREIGN PATENT DOCUMENTS

| | | |
|---|---|---|
| 1467869 | 1/1969 | Fed. Rep. of Germany. |
| 1467871 | 1/1969 | Fed. Rep. of Germany. |
| 1492024 | 1/1969 | Fed. Rep. of Germany. |
| 1577310 | 6/1969 | France. |
| 842866 | 7/1960 | United Kingdom. |

OTHER PUBLICATIONS

"Gafac Surfactants", GAF Corp., Technical Bulletin 7543-096, Copyright 1967.
"Transparent Gels", Goldschmiedt, Soap and Chemical Specialties, Apr. 1970, pp. 48, 50, 52, 54, 64.
Mayhew et al., "Phosphate Surfactants–Properties and Uses", Soap & Chemicals Specialties, May 1962, Part II, pp. 81, 167, 169.

Primary Examiner—P.E. Willis, Jr.
Attorney, Agent, or Firm—Frank T. Barber; Richard G. Harrer

[57] ABSTRACT

A facial cleanser especially useful for the removal of eye make-up is disclosed. A combination of mineral oil, certain phosphate esters and high molecular weight carboxy vinyl polymers, in the absence of water, forms a minimally irritating clear gel having a higher rinsability than mineral oil gelled by prior art methods.

13 Claims, No Drawings

ANHYDROUS CLEAR GEL FACIAL CLEANSER

FIELD OF THE INVENTION

This invention relates to facial cleansers wherein mineral oil is the principal active ingredient, and more specifically to gels of mineral oils.

DESCRIPTION OF THE PRIOR ART

Pure mineral oil is a highly effective facial cleanser but it is aesthetically displeasing. It leaves a greasy feel on the skin and is difficult to rinse off. Moreover, it is liquid at room temperatures and difficult to handle by the user.

Because of the disadvantages of pure mineral oil, various ingredients were added to it in the prior art formulations to give the mineral oil a different appearance and feel and to impart specific properties desired by the formulators.

Aluminum stearate and fumed silica are two examples of prior art ingredients used to gel mineral oil. Emulsions which promote rinsability were made with mineral oil in the well-known water-in-oil, oil-in-water and microemulsion systems. These and other systems used in the art are well-known but they did not provide a wholly satisfactory facial cleanser. For one thing, the prior art systems were not self-emulsifying, and it was believed that the presence of water and surfactant was necessary to product self-emulsifying systems.

Another problem with such prior art preparations, particularly those for removing eye make-up, is that the desired combination of properties: clear gel, good cleansing power, good rinsability and minimal human tissue irritation, is not achieved in a single preparation. For example, the standard water and water/alcohol clear gels using phosphate esters as a microemulsive agent for mineral oil lack the desired cleaning power and are irritating to the eyes. Moreover, to keep this system in a microemulsion ( clear gel form) for longer shelf life, additional surfactants and auxiliary substances, e.g., alcohol, are needed, increasing the irritative effect of the preparation. On the other hand, raising the concentration of oil reduces the irritative effect, but opacifies the gel.

Gels with carboxyvinyl polymers formulated with water or water/alcohol systems cannot be formulated so as to be both effective and minimally irritating to the eyes.

These problems are well-known to workers in the art and brief mention of them will serve to focus attention on the advantages of this invention.

SUMMARY OF THE INVENTION

It has been discovered that certain phosphate esters, when added to a mixture of mineral oil and carboxy vinyl polymers, will produce an anhydrous clear gel which is minimally irritating to human tissue, has greater rinsability than mineral oil gelled by other methods, is self-emulsifying, and has a cleansing efficacy equal to that of pure mineral oil.

It was an unexpected finding of this invention that the phosphate ester caused the carboxy vinyl polymer to thicken the mineral oil without the addition of a fat soluble neutralizing agent, while at the same time conferring rinsability to the solution.

Thus, all of the previously discussed desirable properties have been combined in one product. No auxiliary surfactants are necessary and the need for water and alcohol are dispensed with. The essential ingredients — mineral oil, phosphate ester and carboxy vinyl polymers are further characterized as follows:

The mineral oils used are highly refined, saturated aliphatic hydrocarbons which preferentially are the light mineral oils ranging in viscosity from 48 to 365 Saybolt Seconds, a preferred viscosity range being between about 48 to about 105 Saybolt Seconds. The preparation and properties of mineral oil are further described in *Remington's Practice of Pharmacy*, 11th Edition at pp. 625, 626.

The carboxy vinyl polymer, also known as carboxypolymethylene, is a cross-linked polymer of acrylic acid. It is described in U.S. Pat. No. 2,798,053 issued July 2, 1957 wherein detailed particulars on composition and method of preparation are set forth. Briefly stated, the material is a polymer of acrylic acid which is cross-linked with about 0.75 to about 2% by weight of a polymer, preferably about 1%, of a co-polymerized polyalkenyl polyether. The polymerization of the monomers ordinarily is carried out in an inert hydrocarbon diluent with a free-radical catalyst. The preferred cross-linking polyalkenyl polyether monomers are polyallyl sucrose and polyallyl pentaerythritol, desirably containing an average of at least three allyl groups for each molecule of sucrose or pentaerythritol, the allyl groups attached thereto by means of ether linkages. The preferred polyallyl sucrose contains an average of 5 to 6 allyl groups per molecule of sucrose (theoretical maximum is 8 allyl groups) and the preferred polyallyl pentaerythritol contains 4 allyl ether groups per molecule (the theoretical maximum). The carboxypolymethylenes embodied herein are high molecular weight polymers, e.g., usually having a molecular weight greater than 200,000 and preferably greater than 300,000. The most preferred range of molecular weight is between one million and five million. They are recovered from their polymerization media as white powder. Forms of these resins may be obtained from B. F. Goodrich Company under the trademark "Carbopol," and in three different grades: Carbopol 934, Carbopol 940 and Carbopol 941. All are effective in this invention although Carbopol 941 gives the clearest, most satisfactory solutions. The differences in the properties of 934, 940 and 941 are matters of degree, rather than kind, resulting generally in viscosities of differing values. Their molecular weights are in the range of one million to five million.

The remaining essential ingredient of the cleanser preparaton is a phosphate ester having the following structure:

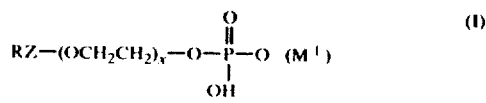

(I)

or

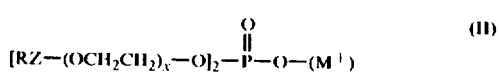

(II)

and mixtures of (I) and (II).

R is a hydrocarbon radical containing 9 to 21 carbon atoms, 0 to 3 double bonds, and it may be straight or branched chained. Z may be any one of the following groups:

$$-CH_2-,-\overset{O}{\underset{\|}{C}}-,-C_6H_4-,-NH-,-\underset{\underset{R''}{|}}{N}-,-\underset{\underset{O}{\|}}{\overset{\overset{O-}{|}}{S}}-,$$

$$-\overset{O}{\underset{\|}{C}}-\underset{\underset{H}{|}}{N}-,-\underset{\underset{O}{\|}}{\overset{\overset{O-}{|}}{S}}-\underset{\underset{H}{|}}{N}-.$$

$M^+$ is a univalent metal ion, preferably sodium and x is a number (on average) from 1 to 10 depending on the size of R such that the phosphate is soluble in the oil to at least 7% by weight.

The moiety RZ $-(OCH_2CH_2)_x$ is derived from a non-ionic detergent which has been formed by ethoxylation of a precursor containing an active hydrogen. The precursor should contain at least six carbon atoms, examples of which are alcohols, phenols, thiols, primary and secondary amines, and carboxylic and sulfonic acids and their amides. These structures are fully defined in U.S. Pat. Nos. 3,004,056 and 3,331,896, assigned to GAF Corporation. A preferred precursor is oleyl or cetyl alcohol and oleyl alcohol is most preferred. In the latter case x = 3 and the preferred compound is the mixture of (I) and (II) set out above, the metal ion being sodium. This material can be obtained from the Croda Company as Crodafos N3 Neut.

A useful range of formulation in this invention is:

| Material | % by weight |
|---|---|
| Mineral oil | 96.9–49.5 |
| Phosphate ester | 3–50 |
| Carboxy vinyl polymer | 0.1–5.0 |
| *Perfume | q.s. |
| *Color | q.s. |
| *Alternate oils | q.s. |

*optional ingredients

A preferred formulation range is:

| Material | % by weight |
|---|---|
| Mineral oil | 87.4–92.7 |
| Phosphate ester | 7–12 |
| Carboxy vinyl polymer | 0.3–0.6 |
| *Perfume | q.s. |
| *Color | q.s. |
| *Alternate oils | q.s. |

*optional ingredients

Inclusion of other materials such as perfume, alternate oils, and the like, depends upon the requirements of the formulator which lie outside the limitations of this invention.

DESCRIPTION OF THE PREFERRED EMBODIMENTS

Starting Materials

The starting materials for a preferred embodiment of this invention are:

A white mineral oil from a natural petroleum source having a viscosity between about 65 and about 75 Saybolt Seconds; Crodafos N3 Neut, and Carbopol 941.

The above ingredients are combined in the following properties by weight: mineral oil 89.5; Crodafos N3 Neut. 10.0; Carbopol 941, 0.5, and stired together at room temperature and atmospheric pressure until thoroughly dispersed. The initial viscosity of the resulting product will be approximately 10 cps (measured with Brookfield RV). The final viscosity will be about 5,000 cps. This formulation is a clear gel — thick and easy to apply, has excellent make-up and dirt removal power, is minimally irritating and is very easily rinsed off the skin.

The following examples serve further to illustrate the invention.

EXAMPLE NO. 1

These formulations were prepared by dissolving the phosphate ester in mineral oil, slowly adding the carboxy vinyl polymer and stirring the ingredients together at room temperature and atmospheric pressure for several hours until a clear light amber gel was formed:

| Material | % by Weight |
|---|---|
| Crodafos N3 Neutral | 8.0 |
| Carbopol 941 | 0.3 |
| Mineral Oil (65/75 Saybolt Sec.) | 91.7 |

Viscosity - 1,800 cps

EXAMPLE NO. 2

Using the process of Example 1, the following formulation was prepared:

| Material | % by Weight |
|---|---|
| Crodafos N3 Neutral | 7.5 |
| Carbopol 941 | 0.3 |
| Mineral Oil (65/75 Saybolt Sec.) | 82.3 |
| Isopropyl palmitate | 10.0 |

EXAMPLE NO. 3

Using the process of Example 1 with the addition of preservative, protein, color, pearlescing agent and perfume, the following gel was made:

| Material | Weight Percent |
|---|---|
| Carnation Mineral Oil | 88.46 |
| Crodafos N3 neutral | 9.96 |
| Carbopol 941 | 0.50 |
| *n-Propyl-p-Hydroxybenzoate | 0.10 |
| **Wilson 1000C | 0.05 |
| 0.1% FD&C Green #6 in Mineral Oil | 0.50 |
| +PF 582-026 | 0.40 |
| ++Mearlmaid OL | 0.03 |

Initial viscosity - 8,600 cps
*n-Propyl-p-Hydroxybenzoate is a commonly used preservative
**Wilson 1000C is a polypeptide derived from collagen
+PF 582-026 is a perfume
++Mearlmaid OL is a pearlescing agent derived from fish scales (guanine based material)

The composition of Example No. 3 is a pearlized light blue gel which turns into a white cream on contact with water. Cleansing properties are excellent and rinse-off is good. Skin irritation is minimal.

The product was found to be stable in all respects. The following viscosities were measured #4 spindle 20 rpm.

| | | |
|---|---|---|
| Initial viscosity | = | 8,600 cps |
| Viscosity after 12 weeks ambient | = | 8,200 cps |
| Viscosity after 12 weeks 100° F | = | 8,550 cps |
| Viscosity after 12 weeks 40° F | = | 8,000 cps |
| Viscosity after 3 freeze-thaw cycles | - | 8,800 cps |

Color after one month under mercury vapor lamp showed slight change but unnoticeable unless compared with standard; pearlescence was unchanged after 5 months standing.

EXAMPLE NO. 4

Using the process of Example 1 the following formulation is prepared:

| Material | % by weight |
| --- | --- |
| Crodafos N3 neutral | 8.0 |
| Carbopol 934 | 0.3 |
| Mineral Oil (65/75 Saybolt Sec.) | 91.7 |

EXAMPLE NO. 5

Using the process of Example 1 the following formulation is prepared:

| Material | % by weight |
| --- | --- |
| Crodafos N3 neutral | 8.0 |
| Carbopol 940 | 0.3 |
| Mineral Oil (65/75 Saybolt Sec.) | 91.7 |

EXAMPLE NO. 6

Using the process of Example 1 the following formulation is prepared:

| Material | % by weight |
| --- | --- |
| Crodafos N3 Neutral | 8.0 |
| Mineral Oil (65/75 Saybolt Sec.) | 91.7 |
| Carboxy vinyl polymer (molecular weight about 200,000) | 0.3 |

EXAMPLE NO. 7

Using the process of Example 1 the following formulation is prepared:

| Material | % by weight |
| --- | --- |
| Crodafos N3 Neutral | 8.0 |
| Mineral Oil (65/75 Saybolt Sec.) | 91.7 |
| Carboxy vinyl Polymer (molecular weight about 500,000) | 0.3 |

The compositions of Examples 4 through 7 are clear gels which turn into a white cream on contact with water. Cleansing properties are excellent and rinse off is good. Skin irritation is minimal. The product has good stability.

Although only selected embodiments of this invention have been described, other variations and equivalent formulations will occur to those skilled in the art, all of which variations and equivalents are within the spirit of this invention.

This invention is to be limited only by the scope of the attached claims, wherein what is claimed is:

1. A composition of matter for use as a facial cleanser, consisting essentially of an anhydrous mixture of:
(a) about 97 to about 49.5 parts by weight of mineral oil;
(b) about 3 to about 50 parts by weight of at least one phosphate ester selected from the group consisting of compounds having the structure

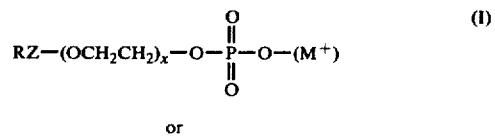

or

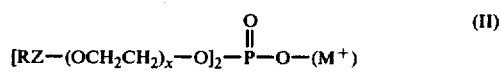

and mixtures thereof wherein $M^+$ is a univalent metal cation; R is a straight branched chain hydrocarbon radical containing 9 to 21 carbon atoms and 0 to 3 double bonds; Z is a member of the group consisting of

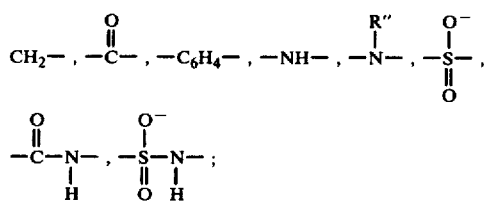

and x is any number (on an average) from 1 to 10 sufficient to maintain the solubility requirement, depending on the value of R;
(c) about 0.1 to about 5 parts by weight of a high molecular weight carboxy vinyl polymer comprised of acrylic acid which is cross-linked with a polymer of a co-polymerized polyalkenyl polyether, said mixture being a clear gel and said phosphate compound being soluble in said oil to at least 7% by weight.

2. The composition of claim 1 wherein said mineral oil is a white mineral oil ranging in viscosity from about 48 to about 365 Saybolt Seconds.

3. The composition of claim 1 wherein said mineral oil is a white mineral oil ranging in viscosity from about 48 to about 105 Saybolt Seconds.

4. The composition of claim 1 wherein the moiety $RZ-(OCH_2CH_2)_x$ is derived from a nonionic detergent which has been formed by ethoxylation of a precursor containing an active hydrogen and at least 6 carbon atoms.

5. The composition of claim 4 wherein said precursor is a compound selected from the class consisting of alcohols, phenols, thiols, primary and secondary amines, and carboxylic and sulfonic acids and their amides.

6. The composition of claim 4 wherein said precursor is selected from the group consisting of oleyl alcohol and cetyl alcohol.

7. The composition of claim 1 wherein said precursor is oleyl alcohol, x = 3 and $M^+$ is a sodium ion.

8. The composition of claim 1 wherein said carboxy vinyl polymer is cross-linked with about 0.75 to about 2% by weight of a co-polymerized polyalkenyl polyether derived from polyallyl sucrose or polyallylpentaerythritol, containing an average of at least three allyl groups for each molecule of sucrose or pentaerythritol, the allyl groups being attached by means of ether linkages.

9. The composition of claim 8 wherein said carboxy vinyl polymer is cross-linked with about 1% by weight of said co-polymerized polyalkenyl polyether.

10. The composition of claim 1 wherein the percentage by weight of said mineral oil is between about 87.4 to about 92.7, the percentage by weight of said phosphate ester is between about 7 and about 12, the percentage by weight of said carboxy vinyl polymer is between about 0.3 and about 0.6.

11. The composition of claim 1 wherein said constituents consist essentially of from about 96.9 to about 49.5 weight percent mineral oil, from about 3 to about 50 weight percent phosphate ester and from about 0.1 to about 5.0 weight percent carboxy vinyl polymer, with the addition of perfume and color.

12. The composition of claim 1 wherein said carboxy vinyl polymer has a molecular weight greater than 200,000.

13. The composition of claim 1 wherein said carboxy vinyl polymer has a molecular weight between about one million and about five million.

* * * * *